US008633975B2

(12) United States Patent  
Amling

(10) Patent No.: US 8,633,975 B2  
(45) Date of Patent: Jan. 21, 2014

(54) NETWORK BASED ENDOSCOPIC SURGICAL SYSTEM

(75) Inventor: Marc R. Amling, Santa Barbara, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 1303 days.

(21) Appl. No.: 12/015,071

(22) Filed: Jan. 16, 2008

(65) Prior Publication Data

US 2009/0179985 A1 Jul. 16, 2009

(51) Int. Cl.
*A62B 1/04* (2006.01)

(52) U.S. Cl.
USPC ............. 348/65; 709/223; 709/226; 709/227; 600/106; 600/108; 600/109; 600/113

(58) Field of Classification Search
USPC .............. 348/65; 600/101; 709/223, 226, 227
See application file for complete search history.

(56) References Cited

U.S. PATENT DOCUMENTS

| | | | | |
|---|---|---|---|---|
| 5,217,003 | A | 6/1993 | Wilk | 128/4 |
| 5,217,453 | A | 6/1993 | Wilk | 606/7 |
| 5,500,854 | A | 3/1996 | Uotila | 370/17 |
| 5,608,446 | A * | 3/1997 | Carr et al. | 725/114 |
| 5,655,084 | A * | 8/1997 | Pinsky et al. | 705/3 |
| 6,282,206 | B1 * | 8/2001 | Hindus et al. | 370/468 |
| 6,351,678 | B1 | 2/2002 | Borders | 700/83 |
| 6,397,286 | B1 | 5/2002 | Chatenever et al. | 710/302 |
| 6,490,490 | B1 | 12/2002 | Uchikubo et al. | 700/65 |
| 6,496,099 | B2 | 12/2002 | Wang et al. | 340/3.7 |
| 6,581,117 | B1 | 6/2003 | Klein et al. | 710/110 |
| 6,612,984 | B1 | 9/2003 | Kerr, II | 600/300 |
| 6,638,218 | B2 | 10/2003 | Bulat | 600/300 |
| 6,642,836 | B1 | 11/2003 | Wang et al. | 340/3.54 |
| 6,645,142 | B2 | 11/2003 | Braig et al. | 600/300 |
| 6,646,541 | B1 | 11/2003 | Wang et al. | 340/3.54 |
| 6,656,115 | B1 | 12/2003 | Miyazaki et al. | 600/300 |
| 6,665,385 | B2 | 12/2003 | Rogers et al. | 374/106.02 |
| 6,685,633 | B2 | 2/2004 | Albert et al. | 600/300 |
| 6,928,490 | B1 | 8/2005 | Bucholz et al. | 709/249 |
| 7,257,932 | B2 * | 8/2007 | Ng | 52/634 |
| 8,069,420 | B2 | 11/2011 | Plummer | |
| 2001/0037508 | A1 * | 11/2001 | Hindus et al. | 725/105 |

(Continued)

FOREIGN PATENT DOCUMENTS

EP 1 172 064 A2 7/2001
EP 1181897 A2 2/2002

(Continued)

OTHER PUBLICATIONS

European Search Report; Application No. EP 09 15 0544; Dec. 1, 2010; 8 pages.

*Primary Examiner* — Tauqir Hussain
(74) *Attorney, Agent, or Firm* — St. Onge Steward Johnston & Reens LLC

(57) ABSTRACT

A network based surgical system including a first medical device having a first network interface, a second medical device having a second network interface, a communications network over which the first medical device, through the first network interface, and the second medical device, through the second network interface, are communicable, wherein the first network interface and the second network interface employ the same network protocol for communicating over the communications network, and wherein the first network interface has a maximum throughput greater than a maximum throughput of the second network interface.

26 Claims, 3 Drawing Sheets

(56) References Cited

U.S. PATENT DOCUMENTS

| | | |
|---|---|---|
| 2002/0133061 A1 | 9/2002 | Manetta ................. 600/300 |
| 2002/0147390 A1 | 10/2002 | Markis et al. ............ 600/301 |
| 2004/0143677 A1 | 7/2004 | Novak ..................... 709/238 |
| 2005/0216252 A1* | 9/2005 | Schoenbach et al. ........ 704/3 |
| 2006/0100610 A1* | 5/2006 | Wallace et al. ............. 606/1 |
| 2006/0149418 A1 | 7/2006 | Anvari |
| 2007/0043338 A1* | 2/2007 | Moll et al. ................... 606/1 |
| 2007/0050828 A1* | 3/2007 | Renzi et al. ............... 725/93 |
| 2007/0197896 A1* | 8/2007 | Moll et al. ................ 600/407 |
| 2007/0199043 A1* | 8/2007 | Morris ..................... 725/143 |
| 2007/0280290 A1* | 12/2007 | Hindus et al. ............ 370/468 |
| 2008/0249401 A1* | 10/2008 | Watanabe et al. ......... 600/437 |
| 2008/0317069 A1* | 12/2008 | Huang et al. ............. 370/503 |
| 2009/0027490 A1* | 1/2009 | Hirai et al. ................ 348/65 |
| 2009/0123111 A1* | 5/2009 | Udd ........................... 385/13 |
| 2011/0238083 A1* | 9/2011 | Moll et al. ................ 606/130 |
| 2012/0065467 A1* | 3/2012 | Moll et al. ................ 600/106 |
| 2012/0209174 A1* | 8/2012 | Moll et al. ............... 604/95.01 |
| 2013/0085397 A1* | 4/2013 | Ramamurthy et al. ....... 600/476 |
| 2013/0090528 A1* | 4/2013 | Ramamurthy et al. ....... 600/117 |
| 2013/0090530 A1* | 4/2013 | Ramamurthy et al. ....... 600/182 |
| 2013/0090552 A1* | 4/2013 | Ramamurthy et al. ....... 600/424 |

FOREIGN PATENT DOCUMENTS

| | | |
|---|---|---|
| WO | WO 00/72180 A2 | 11/2000 |
| WO | 02057877 A2 | 7/2002 |
| WO | 2005006237 A2 | 1/2005 |
| WO | 2007073420 A1 | 6/2007 |
| WO | 2007137115 A2 | 11/2007 |

* cited by examiner

NETWORK BASED ENDOSCOPIC SURGICAL SYSTEM

FIELD OF THE INVENTION

The invention relates to network based surgical systems, and more specifically to a network based endoscopic surgical system including a standardized communication protocol capable of transferring uncompressed digital video.

BACKGROUND OF THE INVENTION

Prior art surgical systems typically comprise a plurality of differing communication protocols and hardware depending upon the type of, and amount of, data being transmitted. For example, systems utilizing lower bandwidth (e.g., 100 Mbs or less) connections have been used for communication between equipment, and lack the speed to transmit digital video data to, and from, cameras, surgical displays, storage devices, control stations, computer networks, and the like. Separate higher bandwidth connections are then also required. This necessitates utilizing one type of connection hardware and its corresponding protocols for command, control, and status functions, and another type of connection hardware and its corresponding protocols for video transmission.

U.S. Pat. No. 6,928,490 discloses a networking infrastructure for an operating room including a plurality of medical devices, each of which is connected through a single communication channel to the network. However, the '490 patent does not provide a system that accommodates devices and network interfaces with different maximum throughputs using a single communication protocol. The '490 patent also does not disclose such a system capable of providing uncompressed streaming video.

It is therefore desired to provide a network based surgical system having a single communication protocol. It is further desired to provide a network based surgical system capable of streaming uncompressed digital video.

SUMMARY OF THE INVENTION

Accordingly, it is an object to provide a network based surgical system for providing individual equipment command and control, individual equipment status and the transfer of uncompressed digital video signals.

It is a further object to provide a network based surgical system having standardization for device connectivity and protocol standardization.

It is a further object of the present invention to provide a network based surgical system including a high speed Ethernet network utilizing commercially available protocols.

It is a further object to provide a system including routing and switching capability, which can isolate each network device (e.g., cameras, display devices, PCs, printers, device controllers and surgical instruments, such as endoscopes and the like).

These and other objectives are achieved by providing a network based surgical system including a first medical device having a first network interface, a second medical device having a second network interface, a communications network over which the first medical device, through the first network interface, and the second medical device, through the second network interface, are communicable, wherein the first network interface and the second network interface employ the same network protocol for communicating over the communications network, and wherein the first network interface has a maximum throughput greater than a maximum throughput of the second network interface. The same network protocol may be, e.g., Ethernet, Gigabit Ethernet, 10 gigabit Ethernet, or 100 gigabit Ethernet.

Other objects are achieved by providing a network based surgical system including a video camera having a first network interface, two or more medical devices each having a second network interface, a communications network over which the video camera, through the first network interface, and the second medical devices, through the second network interfaces, are communicable, wherein the communications network includes at least one switch for sending and receiving data between each of the video camera and two or more medical devices, wherein the first network interface and the second network interface employ the same commercially available network protocol for communicating over the communications network, and wherein the first network interface has a maximum data rate greater than a maximum data rate of the second network interfaces.

Other objects of the invention and its particular features and advantages will become more apparent from consideration of the following drawings and accompanying detailed description.

DETAILED DESCRIPTION OF THE INVENTION

Figure 1:
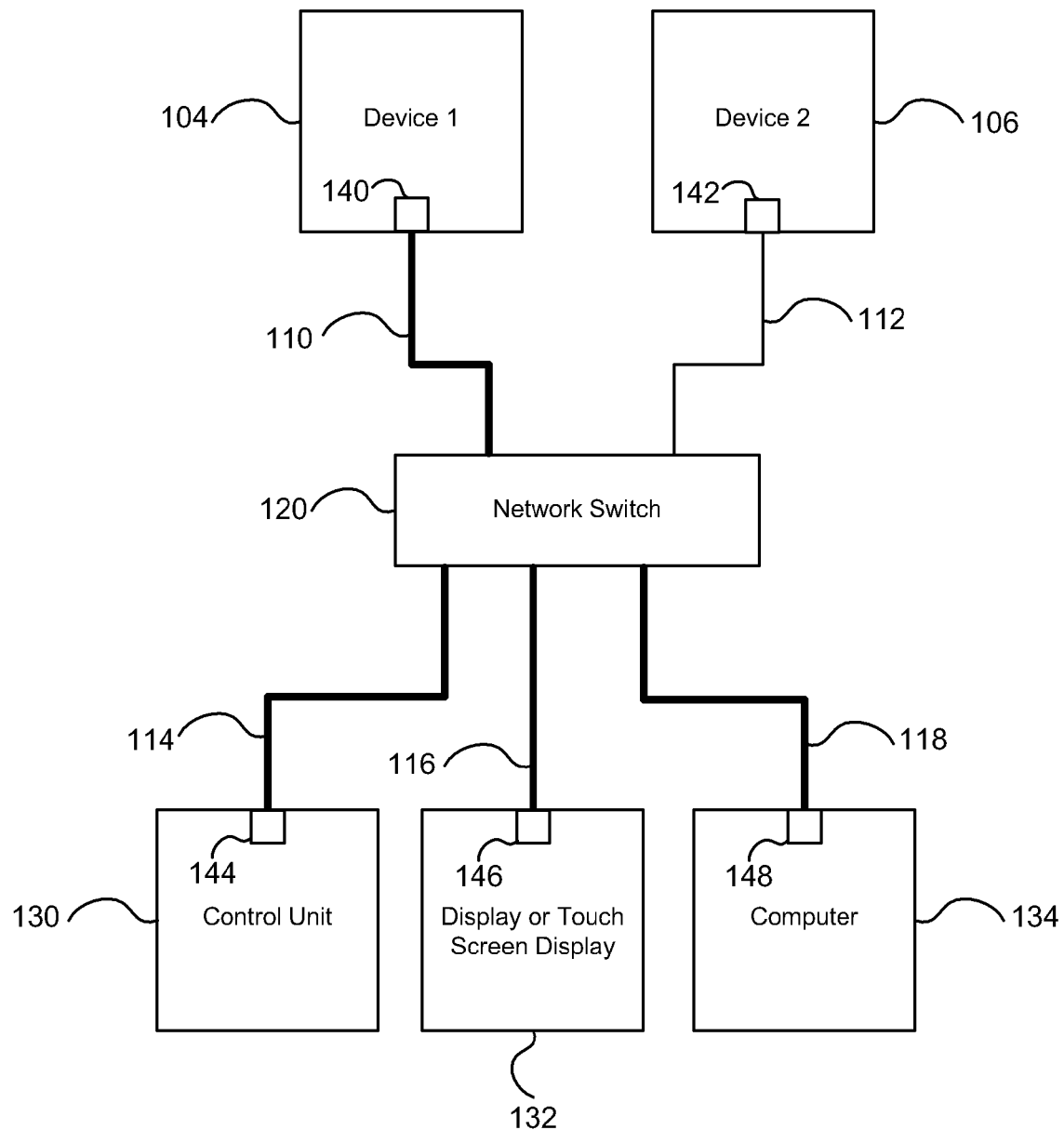
FIG. 1 is a block diagram of one exemplary embodiment of the present invention.

FIG. 1 shows an exemplary embodiment of a system according to the present invention. The system includes one or more medical devices and/or operating room devices (e.g., 104-106, 130-134). The medical devices may comprise, for example, endoscopes, endoflators, thermoflators, light sources, electro-surgical units, operating room cameras, and/or endoscope cameras. The operating room devices may also include device control units 130, camera control units 131, display devices (to include touch screen displays) 132, music players, computers 134, nurses' stations (e.g., personal computers), servers, printers 136, data storage devices, microprocessors, microcontrollers and/or embedded controllers, environmental controllers, surgical tables, telecommunication controllers, hospital information systems, etc.

The medical and/or operating room devices according to the present invention include network interfaces (e.g., 140-150) for communicating via a communication network of the system. For example, a medical and/or operating room device may include a built-in or external network card, network adapter or NIC (network interface card). The network interfaces are preferably Ethernet network interfaces; however, any commercially available high-speed interface may be utilized. Each of the media devices may also include an address (e.g., MAC address) to enable communications to and from other devices in the network. By means of the network interfaces and a common communication protocol, each of the medical and/or operating room devices only requires a network connection and therefore does not require separate connections for different types of data and bandwidths.

The network interfaces for various medical and/or operating room devices may have different maximum throughputs or maximum bandwidths. For example, a network interface for a camera may have a high maximum throughput (e.g., 1 gigabit/sec or more). In some embodiments, a network interface of the present invention has a throughput of 10 gigabit/second ("Gbit/sec"), 100 Gbit/sec, or more. Other network interfaces of the system have lower throughputs, such as less than 1 Gbit/sec or less than 100 megabit/second ("Mbit/s"). However, the network interfaces employ the same network protocol for communicating over the communications network. One lower layer is used to provide all required bandwidth capabilities. Each of the medical and/or operating room devices may further include separate or common power supply couplings (not shown); for example, "Power Over Ethernet" applications.

The system may further include at least one network switch 120 including any number of ports. The switch 120 is preferably an Ethernet network switch supporting both low bandwidths (e.g., 10 Mbit/s, 100 Mbit/s, etc.) as well as high bandwidths (e.g., 1 Gbit/s or more). Each of the medical devices is connectable to a port of the network switch 120 or direct to other devices via a coupling (e.g., 110-120). The couplings of the system may be, for example, twisted pair, copper cabling, InfiniBand, fiber optic, and/or wireless. In some embodiments, the couplings may be selected in accordance with IEEE standards for pertaining to Gigabit Ethernet, 10 gigabit Ethernet, and/or 100 gigabit Ethernet. The switch 120 receives and/or inspects data or data packets (e.g., html format), determines a source and destination device, and forwards the data according. The network switch 120 provides capability to isolate each piece of equipment or medical device from the other on the network via a plurality of channels. Thus, if one channel fails (e.g., cable shorting, component failure, etc.) the remaining communication channels are unaffected.

Figure 2:
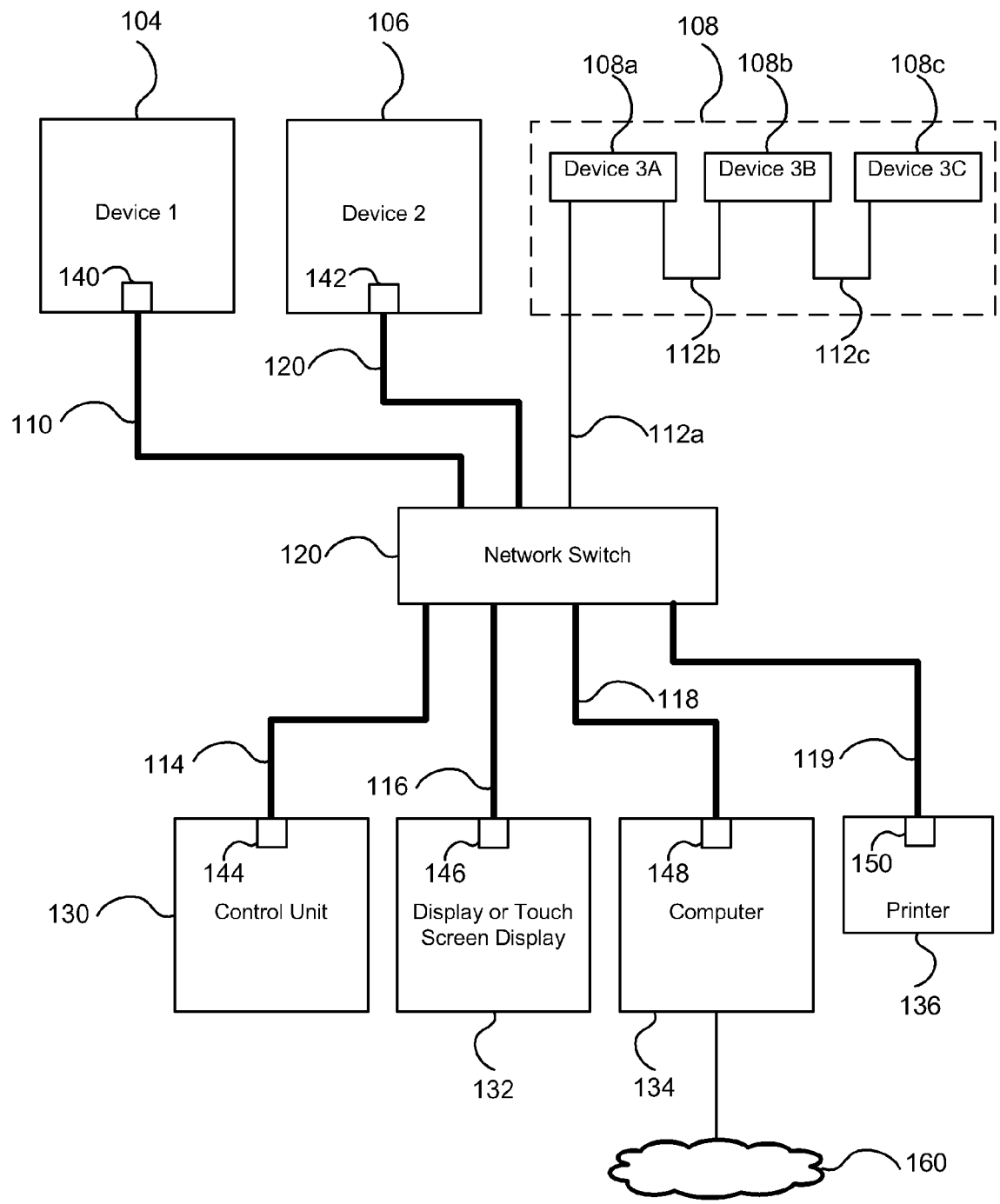
FIG. 2 is another block diagram of the exemplary embodiment according to FIG. 1.

FIG. 2 shows another exemplary embodiment of the system according to the present invention. The system may include one or more subnetworks of medical devices such as subnetwork 108. The subnetwork 108 includes a plurality of devices (e.g., slave devices) connectable in series. For example, the devices 108a-108c may include a light source, an endoflator, a thermoflator and/or an electro-surgical unit.

The system can also be connected to other, possibly remote, medical devices and networks via local area networks, wide area networks or the Internet 160, either wirelessly or by direct connection.

Figure 3:
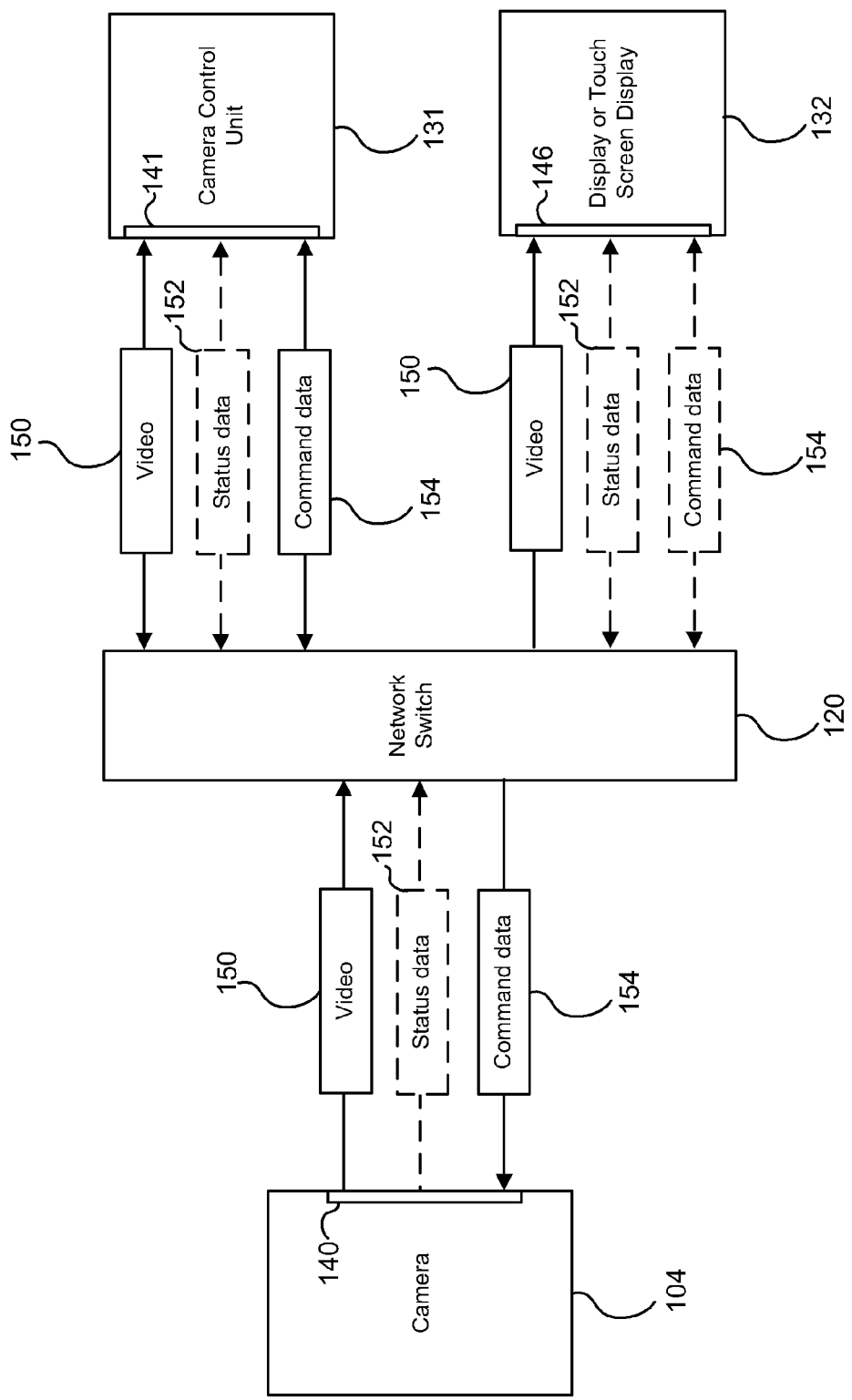
FIG. 3 is another block diagram of the exemplary embodiment according to FIG. 1.

FIG. 3 shows an exemplary embodiment of the system wherein at least one of the medical devices is a camera 104 for generating video data 150. The camera 104 may be, for example, a standard definition (SD) camera or preferably a high definition (HD) camera. In some embodiments, the camera 104 is coupled to or comprised in an endoscope to capture video imagery and/or assist in a medical procedure. The camera 104 may also be an operating room camera.

The camera 104 captures video imagery and transmits or streams uncompressed video data 150 via the network. In some embodiments, the uncompressed video data 150 is high definition video data. The video data 150 is sent to a display 132 or other devices in communication with the particular operating room network or via an external network 160 or Internet. The video data 150 is preferable streamed at 1 Gbit/sec or more. The camera 104 may also receive send and receive status data 152 and command data 154 (e.g., in html format). Data communicated by the system according to the present invention, such as the video data 150, status data 152 and command data 154, is preferably addressed to particular Ethernet address(es) of one or more of the medical devices.

Data sent and received in the system according to the present invention, such as video data 150, is typically packetized and sent (e.g., streamed) using the same lower layer protocol. The system preferable uses an Ethernet protocol (e.g., Gigabit Ethernet, 10 gigabit Ethernet, 100 gigabit Ethernet). Other lower layer protocols employed by the system may include a synchronous optical networking protocol (SONET), synchronous digital hierarchy (SDH), or Wi-Fi. Non-packetized protocols, such as asynchronous transfer mode (ATM) or dynamic synchronous transfer mode (DTM), either utilizing packetized or non-packetized transmission techniques, may be implemented in some embodiments.

The camera 104 may further be in communication with a camera control unit (CCU) 131. The CCU may, for example, be of the type described in commonly owned U.S. patent application Ser. No. 11/695,960, the specification of which is incorporated herein by reference. The CCU 131 captures and/or processes the uncompressed video data 150. The CCU 131 may also send and receive status data 152 and command data 154, e.g., to operate and adjust camera settings, via the operating room network. For example, the CCU 131 provides command data 154 to control the camera by adjusting color balance, light, focal distance, resolution, zoom, focus, shading, and other types of optical characteristics. The CCU 131 may also receive command data 154 from any number of input devices and/or computers.

Although the invention has been described with reference to a particular arrangement of parts, features and the like, these are not intended to exhaust all possible arrangements or features, and indeed many modifications and variations will be ascertainable to those of skill in the art.

What is claimed is:

1. A network based surgical system comprising:
a first medical device having a first network interface, the first medical device being an endoscope camera;
a second medical device having a second network interface, the second medical device being one of an endoflator, a thermoflator, an electro-surgical unit, and a surgical table;
a communications network over which said first medical device, through the first network interface, and said second medical device, through the second network interface, are communicable;
wherein the first network interface and the second network interface employ a single Ethernet protocol for communicating device command data and video data over said communications network, wherein said single Ethernet protocol is one of Gigabit Ethernet, 10 gigabit Ethernet, and 100 gigabit Ethernet; and
wherein the first network interface has a maximum throughput of at least 1 gigabit/second and greater than a maximum throughput of the second network interface.

2. The system according to claim 1, wherein the maximum throughput of the first network interface is at least 10 gigabit/second.

3. The system according to claim 1, wherein the maximum throughput of the first network interface is at least 100 gigabit/second.

4. The system according to claim 1, wherein the maximum throughput of the second network interface is less than 1 gigabit/second.

5. A network based surgical system comprising:
a first medical device having a first network interface, the first medical device being an endoscope camera;
a second medical device having a second network interface, the second medical device being one of an endoflator, a thermoflator, an electro-surgical unit, and a surgical table;

a communications network over which said first medical device, through the first network interface, and said second medical device, through the second network interface, are communicable;

wherein the first network interface and the second network interface employ a single network protocol for communicating device command data and video data over said communications network;

wherein the first network interface has a maximum throughput greater than a maximum throughput of the second network interface;

wherein said first medical device is a video camera; and wherein said first medical device streams uncompressed video data via the first network interface to said communications network at a data rate of at least 1 gigabit/second.

6. The system according to claim 5, wherein said second medical device is a camera control unit for receiving the video data and is in communication with said camera.

7. The system according to claim 1, further comprising:
at least one network switch connectable to each of the first and second network interfaces via a coupling.

8. The system according to claim 7, wherein the coupling is a fiber optic coupling.

9. The system according to claim 1, further comprising:
at least one subnetwork having a third network interface for communicating with said communications network, said subnetwork including two or more connected medical devices.

10. The system according to claim 1, further comprising:
at least one subnetwork having a third network interface for communicating with said communications network, said subnetwork including two or more connected operating room devices.

11. A network based surgical system comprising:
an endoscopic video camera having a first network interface;
two or more medical devices each having a second network interface, the two or more medical devices including at least one of an endoflator, a thermoflator, an electrosurgical unit, and a surgical table;
a communications network over which said video camera, through the first network interface, and said second medical devices, through the second network interfaces, are communicable;
wherein said communications network includes at least one network switch for sending and receiving data between the video camera and two or more medical devices;
wherein the first network interface and the second network interface employ a single network protocol for communicating device command data and video data over said communications network; and
wherein the first network interface has a maximum data rate greater than a maximum data rate of the second network interfaces; and
wherein the maximum data rate of the first network interface is at least 1 gigabit/second;
wherein said video camera streams uncompressed digital video data via said communications network.

12. The system according to claim 11, wherein said video camera provides the uncompressed video data at a first data rate to said switch and said two or more medical devices provide data to said switch at a second data rate, wherein the first rate is greater than the second rate.

13. The system according to claim 11, wherein said video camera provides compressed video data at a first data rate to said switch and said two or more medical devices provide data to said switch at a second data rate, wherein the first rate is greater than the second rate.

14. The system according to claim 11, wherein the data sent and received between each of the video camera and two or more medical devices includes packetized data.

15. The system according to claim 11, wherein the data sent and received between each of the video camera and two or more medical devices includes unpacketized data.

16. The system according to claim 11, wherein said video camera provides compressed video data to said communications network at a data rate of at least 1 gigabit/second.

17. The system according to claim 11, wherein said video camera is a high definition video camera.

18. The system according to claim 1, wherein the first medical device includes a first address and the second medical device includes a second address to enable communications to and from other devices over the communications network.

19. The system according to claim 5, wherein the single network protocol is at least one of a synchronous optical networking protocol (SONET) and a synchronous digital hierarchy (SDH).

20. The system according to claim 5, wherein the single network protocol is Wi-Fi.

21. The system according to claim 5, wherein the single network protocol is one of asynchronous transfer mode (ATM) and dynamic synchronous transfer mode (DTM).

22. The system according to claim 5, wherein said single network protocol is an Ethernet protocol wherein the Ethernet protocol is one of Gigabit Ethernet, 10 gigabit Ethernet, and 100 gigabit Ethernet.

23. The system according to claim 11, wherein the single network protocol is one of a synchronous optical networking protocol (SONET) and a synchronous digital hierarchy (SDH).

24. The system according to claim 11, wherein the single network protocol is Wi-Fi.

25. The system according to claim 11, wherein the single network protocol is one of asynchronous transfer mode (ATM) and dynamic synchronous transfer mode (DTM).

26. The system according to claim 11, wherein said single network protocol is an Ethernet protocol, wherein the Ethernet protocol is one of Gigabit Ethernet, 10 gigabit Ethernet, and 100 gigabit Ethernet.

* * * * *